United States Patent [19]

Bernath et al.

[11] 4,113,868
[45] Sep. 12, 1978

[54] 5,6-DIHYDROPYRIMIDIN-4(3H)ONE DERIVATIVES, AND ANTIEDEMA COMPOSITIONS AND METHODS EMPLOYING THEM

[75] Inventors: Gabor Bernath; Lajos Gera; György Göndös, all of Szeged; Zoltan Ecsery; Judit Hermann nee Voros, both of Budapest; Matyas Szentivanyi; Erzsebet Janvari, nee Kanyo, both of Budapest, all of Hungary

[73] Assignee: Chinoin Gyogyszer es Vegyeszeti Termekek Gyara R.T., Budapest, Hungary

[21] Appl. No.: 728,459

[22] Filed: Sep. 29, 1976

[30] Foreign Application Priority Data

Oct. 3, 1975 [HU] Hungary .................................. 1614

[51] Int. Cl.² ............... C07D 239/90; C07D 239/91; A61K 31/505
[52] U.S. Cl. ................................................ 424/251; 560/125; 544/253
[58] Field of Search ............. 260/251 A, 256.4 Q; 424/251

[56] References Cited

U.S. PATENT DOCUMENTS

| 3,047,462 | 7/1962 | Maillard et al. | 260/251 QA |
| 3,631,042 | 12/1971 | Vincent et al. | 260/251 QA |
| 3,696,102 | 10/1972 | Cronin | 260/251 QA |
| 3,945,960 | 3/1976 | Salmond | 260/251 A |
| 3,994,894 | 11/1976 | Salmond | 260/251 A |
| 3,996,227 | 12/1976 | Salmond | 260/251 A |

OTHER PUBLICATIONS

Maillard et al., Chem. Abstracts, 69 36,006q (1968).
Armarego et al., Chem. Abstracts, 74 76,384b (1971).
Kato et al., Chemical Abstracts 75 151,753x (1971).
Brown, Fused Pyrimidines, Interscience Publishers, N.Y. (1967), pp. 87-93.

*Primary Examiner*—Donald G. Daus
*Assistant Examiner*—Diana G. Rivers
*Attorney, Agent, or Firm*—Karl F. Ross

[57] ABSTRACT

An antiedema compound of the formula:

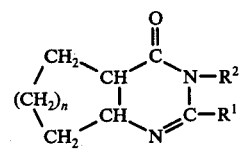

in which
R¹ is methyl, ethyl, cyclohexyl, phenyl, m-tolyl, p-tolyl, p-tert-butylphenyl, m-trifluoromethylphenyl, m-fluorophenyl, p-fluorophenyl, m-chlorophenyl, p-chlorophenyl, m-bromophenyl, p-bromophenyl, o-hydroxyphenyl, p-methoxyphenyl, p-nitrophenyl, benzyl, p-chlorobenzyl, m,p-dimethoxybenzyl, and o-pyridyl;
R² is hydrogen, p-tolyl, p-ethoxyphenyl, m-pyridyl, methyl or phenyl; and
n is 1, 2 or 3 and a process for the preparation thereof are disclosed.

38 Claims, No Drawings

5,6-DIHYDROPYRIMIDIN-4(3H)ONE DERIVATIVES, AND ANTIEDEMA COMPOSITIONS AND METHODS EMPLOYING THEM

The present invention relates to new cis- and trans-5,6-alkylene-5,6-dihydro-pyrimidin-4(3H)-on derivatives of the formula I

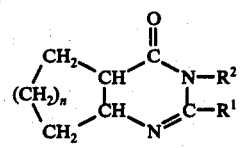

wherein
$R^1$ stands for a lower alkyl, aryl, substituted aryl, aralkyl, or heteroaryl group,
$R^2$ stands for a hydrogen atom, or an alkyl, aryl, substituted aryl, aralkyl, substituted aralkyl or heteroaryl group,
$n = 1, 2$ or $3$.

According to an other aspect of the invention there is provided a method for the preparation of the compounds of the formula I, wherein $R^1$ and $R^2$ have the same meaning as defined above, which comprises reacting 2-aminocycloalkane-carboxylic acid derivatives of the formula II

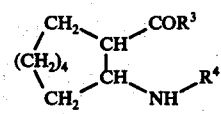

wherein
$R^3$ stands for a hydroxyl, alkoxy or —NH—$R^2$ group, wherein $R^2$ has the same meaning as defined above,
$R^4$ stands for a hydrogen atom, or a

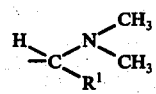

group,
wherein
$R^1$ has the same meaning as defined above,
$n$ has the same meaning as defined above with compounds of the formula III $$A - B \qquad (III)$$

wherein
A stands for a hydrogen atom, an alkoxy or amino group, or a halogen atom,
B represents an —NH—$R^2$,

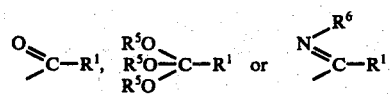

group
$R^5$ stands for an alkyl or aryl group, and
$R^6$ represents a hydrogen atom, an alkyl or aryl group.

There are only a few 5,6-alkylene-5,6-dihydropyrimidin-4(3H)-on derivatives already published. The basic compounds were described by Armarego and Kobayashi in J. Chem. Soc. 1969, 1635 and J. Chem Soc. (C) 1971, 238. The authors prepared, however, the unsubstituted derivatives of tetramethylene-pyrimidin-4(3H)-ons nominated as 4a,5,6,7,8,8a-hexahydroquinazoline-4(3H)-on only, and the pharmacological activity of those compounds has not been even mentioned. It should be noted that the aromatic 4(3H)-on-quinazoline derivatives closely related with the above compounds possess narcotic and anticonvulsive properties. (J. Indian Chem. Soc. 26, 344 (1951), J. Pharmacy and Pharmacology 12, 501 (1960). The 2- and 2- and 3-substituted, 5,6-alkylene-5,6-dihydro-pyrimidin-4(3H)-on derivatives provided by the invention show outstanding antiinflammatory, antifebrile, analgesic and narcosis potentiating activity.

According to a preferred embodiment of the process provided by the invention 2-amino-1-cycloalkane-carboxylic acids of the formula II are reacted with alkyl- or aryl-imidates of the formula III. The imidates may be substituted or unsubstituted as well. In case that they are substituted, i.e. $R^6$ is other than hydrogen, 3-substituted 5,6-alkylene-5,6-dihydro-pyrimidin-4(3H)-on derivatives are obtained. The reaction is carried out preferably in a suitable solvent, with heating. As solvent reaction-inert solvents, for example aromatic hydrocarbons, substituted aromatic hydrocarbons, ethers may be applied. An especially preferred solvent is chlorobenzene. The reaction may be accomplished at a temperature between 20° C and 150° C. The reaction time may vary depending upon the reaction temperature and is between 4 and 30 hours. The progress of the reaction may be controlled by t.l.c. When the reaction is complete the reaction mixture is evaporated and the residue optionally is purified by recrystallization.

According to another embodiment of our process 2-amino-1-cycloalkanecarboxamides of the formula II are reacted with orthoacid-esters of the formula III under the conditions described above. In this case, if the carboxamide is N-substituted, 3-substituted pyrimidine derivatives are prepared.

According to a still further embodiment of our process 2-amino-1-cycloalkanecarboxamides of the formula II are reacted with amidines of the formula III. The reaction is preferably carried out in such a manner that to the mixture of 2-amino-1-cycloalkane-carboxylic acid and a salt of the amidine a calculated amount of alkali- and alkali earth-alcoholate is added in order to deliberate amidin base, and thereafter — if necessary — the reaction is promoted by heating. The reaction mixture is filtered hot and the product is obtained by crystallization of the mixture.

One can proceed also by reacting an ester of 2-amino-1-cycloalkane-carboxylic acid with N,N-dimethyl-formamide-chloride and thus preparing N,N-dimethyl-N-[2-(ethoxy-carbonyl)-cyclohexyl]-formamidine hydrochloride. The reaction is carried out preferably in a solvent.

Examples of suitable solvents are aliphatic and aromatic hydrocarbons, halogenated hydrocarbons and ethers. The reaction temperature is between 0° C and 60° C, and the product is obtained by evaporating the mixture and may be purified by recrystallization. Reacting the thus obtained N,N-dimethyl-N-[2-(ethoxy-carbonyl)-cycloalkyl]-formamidine with ammonia or amines the 5,6-alkylene-5,6-dihydropyrimidin-4(3H)-on derivatives are obtained. During the reaction the reacting amine replaces the dimethylamine split off, whereupon the resulted new formamidine derivative reacts with the vicinal ethoxy-carbonyl group. The ring closure reaction results in the formation of a 5,6-alkylene-5,6-dihydropyrimidin-4(3H)-on derivative and alcohol. The reaction can be effected on dioxane but also other reaction-inert solvents, for example other ethers, hydrocarbons, chlorinated hydrocarbons etc. may be used. The ammonium salts and substituted ammonium salts precipitating during the reaction are filtered off, and the product is obtained by evaporating the reaction mixture and may be purified, if necessary, by various physical methods. A very effective purification method is for example thin layer chromatography.

The above reactions may be effected with the same results using cis- or trans-2-amino-1-cycloalkane-carboxylic acids or their derivatives, but the mixture of the cis- and trans-compounds may be also applied. Further details of our invention are illustrated with the following Examples without limiting the scope of the invention to the Examples.

EXAMPLE 1

Cis- or trans-2-amino-1-cyclohexane-carboxylic acid (0.01 mole) is suspended in chlorobenzene (20 ml) and an ethylimidate derivative (0.012 mole) is added. The reaction mixture is refluxed and the progress of the reaction is followed by thin layer chromatography (silica-gel — benzene — ethanol 4:1). When the reaction is completed (about 15 to 20 hours) the mixture is evaporated under reduced pressure and the residue is crystalized. The characteristics of the thus obtained 2-substituted cis- and trans-4a,5,6,7,8,8a-hexahydroquinazoline-4(3H)-ons are listed in Table 1.

Table 1

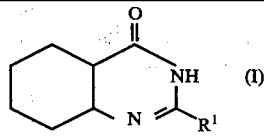
(I)

Melting point and analysis data for 2-substituted 4a,5,6,7,8,8a-hexahydroquinazolin-4(3H)-on (I)

| R¹ | Configuration | Formula molar weight | M.p. °C for the solvent used for crystallisation | Analysis calculated found (%) | | | Yield % | Remark |
|---|---|---|---|---|---|---|---|---|
| | | | | C | H | N | | |
| methyl | cis | $C_9H_{14}N_2O$ 166.22 | 146–148 sublimated | 64.99 64.70 | 8.47 8.78 | 16.85 16.70 | 51.31 | From cis-amide with ortho-esther |
| cyclohexyl | cis | $C_{14}H_{22}N_2O$ 234.33 | 158 ether | 71.75 71.96 | 9.46 9.67 | 11.96 11.63 | 21.80 | when prepared vom cis-acid, mixture may be separated from ether by crystallization |
| phenyl | cis | $C_{14}H_{16}N_2O$ 228.29 | 186–187 chlorobenzene | 73.65 73.20 | 7.02 7.06 | 12.28 12.01 | 84.21 | JATE 57 |
| phenyl | trans | $C_{14}H_{16}N_2O$ 228.29 | 207–209 chlorobenzene | 73.65 73.89 | 7.02 6.95 | 12.28 12.47 | 67.21 | JATE 58 |
| m-tolyl | cis | $C_{15}H_{18}N_2O$ 242.31 | 146–148 chlorobenzene | 74.35 74.41 | 7.49 7.79 | 11.56 11.67 | 69.29 | JATE 118 |
| p-tolyl | cis | $C_{15}H_{18}N_2O$ 242.31 | 171–173 chlorobenzene | 74.35 74.50 | 7.49 7.89 | | 73.21 | JATE 122 from cis-amino acid |
| p-tolyl | trans | $C_{15}H_{18}N_2O$ 242.31 | 222 chlorobenzene | 74.35 74.69 | 7.49 7.89 | 11.56 11.58 | 75.67 | JATE 111 |
| p-tert. butylphenyl | trans | $C_{18}H_{24}N_2O$ 284.40 | 230–231 chlorobenzene | 76.02 76.40 | 8.45 8.32 | 9.85 10.51 | 87.36 | JATE 110 |
| m-trifluoromethyl-phenyl | | $C_{15}H_{15}F_3N_2O$ 296.29 | 164–165 ethanol | 60.81 60.56 | 5.10 5.20 | 9.46 9.35 | 71.32 | JATE 161 from cis-amino acid |
| m-fluorophenyl | cis | $C_{14}H_{15}FN_2O$ 246.29 | 120–123 chlorobenzene | 68.27 68.41 | 6.14 6.43 | 11.37 10.88 | 78.71 | JATE 117 |
| m-fluorophenyl | trans | $C_{14}H_{15}FN_2O$ 246.29 | 213 ethanol | 68.27 68.20 | 6.14 6.29 | 11.37 11.76 | 79.73 | JATE 104 |
| p-fluorophenyl | cis | $C_{14}H_{15}FN_2O$ 246.29 | 191–193 chlorobenzene | 68.27 68.75 | 6.14 6.50 | 11.37 10.95 | 78.47 | JATE 103 |
| p-fluorophenyl | trans | $C_{14}H_{15}FN_2O$ 246.29 | 233 ethanol | 68.27 68.16 | 6.14 6.24 | 11.37 12.15 | 50.00 | |
| m-chlorophenyl | cis | $C_{14}H_{15}ClN_2O$ 262.74 | 162–164 chlorobenzene | 64.01 63.66 | 5.76 5.89 | 10.66 10.95 | 71.30 | JATE 105 |
| p-chlorophenyl | trans | $C_{14}H_{15}ClN_2O$ 262.74 | 211 ethanol | 64.01 64.22 | 5.76 6.10 | 10.66 11.26 | 74.15 | JATE 106 |
| p-chlorophenyl | | $C_{14}H_{15}ClN_2O$ 262.74 | 178–181 ethanol | 64.01 64.25 | 5.76 5.77 | 10.66 10.46 | 68.98 | JATE 83 from cis amino acid |
| p-chlorophenyl | | $C_{14}H_{15}ClN_2O$ 262.74 | 247–249 chlorobenzene | 64.00 64.70 | 5.75 5.85 | 10.65 10.90 | 64.05 | JATE 84 from trans amino acid |
| m-bromophenyl | | $C_{14}H_{15}BrN_2O$ 307.20 | 167–170 ethanol | 54.74 54.56 | 4.92 4.93 | 9.12 9.46 | 79.27 | JATE 107 from cis amino acid |
| m-bromophenyl | trans | $C_{14}H_{15}BrN_2O$ 307.20 | 206–207 ethanol | 54.74 54.72 | 4.92 5.11 | 9.12 9.11 | 64.21 | JATE 108 |
| p-bromophenyl | cis | $C_{14}H_{15}BrN_2O$ 307.20 | 188–193 chlorobenzene | 54.74 55.17 | 4.92 4.89 | 9.12 9.12 | 82.37 | |
| p-bromophenyl | | $C_{14}H_{15}BrN_2O$ 307.20 | 252–253 chlorobenzene | 54.74 54.82 | 4.92 5.14 | 9.12 9.03 | 69.73 | from trans amino acid |
| o-hydroxyphenyl | | $C_{14}H_{16}N_2O_2$ 244.28 | 217–220 ethanol | 68.83 68.54 | 6.60 6.82 | 11.47 12.06 | 67.23 | |
| p-methoxyphenyl | | $C_{15}H_{18}N_2O_2$ | 189–191 | 69.75 | 7.03 | 10.85 | 81.26 | |

Table 1-continued

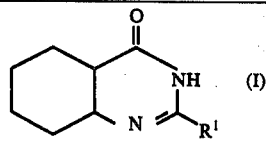

Melting point and analysis data for 2-substituted 4a,5,6,7,8,8a-hexahydroquinazolin-4(3H)-on (I)

| R¹ | Configuration | Formula molar weight | M.p. °C for the solvent used for crystallisation | Analysis calculated found (%) C | H | N | Yield % | Remark |
|---|---|---|---|---|---|---|---|---|
| p-methoxyphenyl | trans | 258.32 $C_{15}H_{18}N_2O_2$ 258.32 | 188-190 chlorobenzene | 70.01 69.75 68.82 | 7.09 7.03 7.38 | 10.67 10.85 10.86 | 71.27 | |
| p-nitrophenyl | | $C_{14}H_{15}N_3O_3$ 273.29 | 202-204 ethanol | 61.53 61.41 | 5.53 5.70 | 15.38 15.06 | 52.15 | from cis amino acid |
| p-nitrophenyl | | $C_{14}H_{15}N_3O_3$ 273.29 | 247-250 benzene | 61.53 61.47 | 5.53 5.83 | 15.38 15.32 | 34.17 | from trans amino acid |
| benzyl | trans | $C_{15}H_{18}N_2O$ 242.32 | 149-151 benzene | 74.40 74.38 | 7.43 7.71 | 11.57 11.60 | 42.47 | from cis amino acid in ether fractionated cryst. |
| p-chlorobenzyl | cis | $C_{15}H_{17}ClN_2O$ 276.77 | 133-135 ethanol-ether | 65.09 65.00 | 6.19 6.46 | 10.12 10.05 | 51.30 | from cis amino acid |
| m,p-dimethoxy-benzyl | trans | $C_{17}H_{22}N_2O_3$ 302.38 | 135-137 benzene | 67.54 67.60 | 7.28 7.17 | 9.27 9.19 | 27.9 | from cis amino acid in ether fractionated cryst. |
| o-pyridyl | | $C_{14}H_{15}N_3O$ 241.29 | 101-103 ether | 69.69 69.13 | 6.27 6.81 | 17.42 17.43 | 37.40 | from trans amino acid |

EXAMPLE 2

Following the procedure of Example 1, reacting cis- or trans-2-amino-1-cycloheptane-carboxylic acid (0.01 mole) in chlorobenzene (20 ml.) with an ethylimidate derivative (0.012 mole) cis- and trans-5,6-pentamethylene-5,6-dihydropyrimidine-4(3H)-on derivatives listed in table 2 are obtained.

TABLE 3

Following the procedure of Example 1, with the reaction of cis- or trans-2-amino-1-cyclohexane-carboxylic acid (0.01 mole) in 20 ml. of chlorobenzene with N-substituted-ethylimidate the cis- and trans-2,3-disubstituted-4a,5,6,7,8,8a-hexahydroquinazoline-4(3H)-on derivatives listed in table 3 are obtained.

Table 2

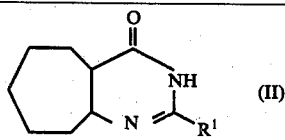

Melting point and analysis data for 2-substituted trans-5,6-pentamethylene-5,6-dihydropyrimidine-4(3H)-on

| R¹ | Configuration | Formula molar weight | M.p. °C for the solvent used for crystallization | Analysis Calculated found C: | H: | N: | Yield % | Remarks |
|---|---|---|---|---|---|---|---|---|
| phenyl | cis | $C_{15}H_{18}N_2O$ 242.32 | 145-146 ethanol | 74.40 73.68 | 7.44 7.36 | 11.56 | 65.17 | |
| phenyl | trans | $C_{15}H_{18}N_2O$ 242.32 | 180-183 ethanol | 74.40 74.40 | 7.44 7.55 | 11.56 | 42.51 | |
| p-tert-butyl-phenyl | | $C_{19}H_{26}N_2O$ 298.36 | 193-197 benzene | 76.51 76.60 | 8.72 9.09 | 9.32 9.66 | 37.15 | from trans amino acid |
| m-chlorophenyl | | $C_{15}H_{17}ClN_2O$ 276.77 | 187-195 ethanol | 65.08 65.02 | 6.19 6.24 | 10.12 9.92 | 33.50 | from trans amino acid |
| p-chlorophenyl | | $C_{15}H_{17}ClN_2O$ 276.77 | 208-209 ethanol | 65.08 65.29 | 6.19 5.85 | 10.12 10.57 | 41.15 | from trans amino acid |
| p-bromophenyl | | $C_{15}H_{17}BrN_2O$ 321.23 | 236 chlorobenzene | 55.94 55.61 | 5.63 5.37 | 8.70 8.74 | 68.10 | JATE 88 from trans amino acid |
| p-nitrophenyl | | $C_{15}H_{17}N_3O_3$ 287.32 | 240-243 chlorobenzene | 62.71 62.66 | 5.96 6.15 | 14.62 14.51 | 38.20 | JATE 90 from trans amino acid |

Table 3

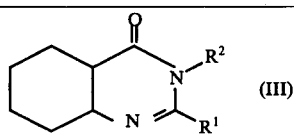
(III)

Melting point and analysis data for 2,3-disubstituted 4a,5,6,7,8,8a-hexahydroquinazoline-4(3H)-one (III)

| R¹ | R² | Configuration | Formula molar weight | M.p. °C for the solvent used for crystallization | Analysis calculated found C: | H: | N: | Yield % | Remark |
|---|---|---|---|---|---|---|---|---|---|
| methyl | p-tolyl | cis | $C_{16}H_{20}N_2O$ 265.34 | 71–74 n-hexane | 74.96 75.13 | 7.86 8.09 | 10.93 10.63 | 37.15 | JATE 169 from acid amide with o-acid-ester |
| methyl | p-ethoxy-phenyl | | $C_{17}H_{22}N_2O_2$ 286.36 | 179–180 ethanol | 71.30 71.03 | 7.74 7.46 | 9.78 9.94 | 32.21 | JATE 170 from acid amide with o-acid-ester |
| methyl | p-ethoxy-phenyl | | $C_{17}H_{22}N_2O_2$ 286.36 | 94–97 ether-petroleum ether | 71.30 70.54 | 7.74 7.56 | | 14.27 | from cis-aminoacid with imino-ether |
| methyl | p-ethoxy phenyl | | $C_{17}H_{22}N_2O_2$ 286.36 | 177–178 ether | 71.30 | 7.74 | | 10.35 | from cis-aminoacid with imino-ether |
| ethyl | m-pyridyl | | $C_{14}H_{17}N_3O$ 243.30 | 115–118 diisopropylether | 69.11 68.64 | 7.04 7.03 | 17.27 16.66 | 31.17 | from acid-amide with o-acid-esther |
| ethyl | p-tolyl | | $C_{17}H_{22}N_2O$ 270.36 | 63–66 n-hexane | 75.52 75-57 | 8.20 8.42 | 10.36 10.64 | 33.27 | from acid amide with o-acid-ester |
| phenyl | methyl | cis | $C_{15}H_{18}N_2O$ 242.32 | 80–82 ether | 74.36 74.80 | 7.49 7.39 | 11.56 11.27 | 21.51 | from cis-with imino-ether |
| phenyl | p-tolyl | | $C_{21}H_{22}N_2O$ 318.40 | 200–203 ethylacetate | 79.21 79.56 | 6.96 7.34 | 8.80 8.63 | 34.35 | from acid amide with o-acid-ester |
| phenyl | phenyl | | $C_{20}H_{20}N_2O$ 304.39 | 180–182 ether | 78.92 78.54 | 6.62 6.27 | 9.20 9.20 | 20.13 | from cis-aminoacid with imino-ether |

EXAMPLE 4

N-substituted 2-amino-1-cyclohexane-carboxamide (0.01 mole) is suspended in chlorobenzene (25 ml.) and boiled with orthoacid ester (0.011 mole) for 8 to 10 hours. The chlorobenzene is distilled off under reduced pressure and the residue is crystallized. The thus obtained 2,3-disubstituted 4a,5,6,7,8,8a-hexahydroquinazoline-4(3H)-on derivatives were set forth in table 3.

EXAMPLE 5 cis-2-Amino-1-cyclopentane-carboxylic acid (12.92 g., 0.1 mole) is boiled with ethylbenzimidate (16.41 g., 0.11 mole) for 20 hours according to the procedure of Example 1. Thus 14.1 g. of 2-phenyl-cis-5,6-trimethylene-5,6-dihydropyrimidine-4-(3H)-on are obtained. Melting point after recrystallization from ethanol: 130° C to 140° C.

Analysis for $C_{15}H_{12}N_2O$; Calculated: C 72.86% H 6.59% N 13.07%; Found: C 73.43% H 6.74% N 13.13%.

EXAMPLE 6 cis-2-Amino-1-cyclohexane-carboxylic acid (1 g., 0.005 mole) and p-methoxy-benzamidine-hydrochloride (1.3 g., 0.005 mole) are suspended in chlorobenzene (50 ml.). To the suspension sodium ethylate (0.4 g., 0.005 mole) is added and then mixture is boiled for 20 hours. Thereafter the resulted sodium chloride and the unreacted amino-acid component are filtered off hot. At 0° C 2-(p-methoxy-phenyl)-cis-4a,5,6,7,8,8a-hexahydroquinazoline-4(3H)-on precipitates, which is filtered off and crystallized from benzene until its melting point is constant.

Yield: 0.8 g., melting point: 188°–191° C.

Analysis for $C_{15}H_{18}N_2O_2$; Calculated: C 69.75% H 7.03% N 10.85%; Found: C 69.91% H 7.11% N 10.68%.

EXAMPLE 7

To the mixture of N,N-dimethyl-formamidechloride (12.99 g., 0.01015 mole) and abs. chloroform (20 ml.) ethyl-(cis-2-amino-1-cyclohexanecarboxylate) (14.32 g., 0.1 mole) in 40 ml. of abs. chloroform is added dropwise, assuring that the reaction temperature does not exceed 40° C. Thereafter chloroform is distilled off and the residue is crystallized from dioxane. 22.38 g. of white, hygroscopic N,N-dimethyl-N-cis-2-(ethoxy-carbonyl)-cyclohexyl-formamidine-hydrochloride are obtained.

Melting point: 137° C to 142° C.

Analysis for $C_{12}H_{23}ClN_2O$; Calculated: C 54.84% H 8.82% N 10.66% Cl 13.4%; Found: C 54.38% H 8.94% N 11.08% Cl 13.55%.

The melting point of the picrate is: 114° C to 116° C.

Analysis for $C_{18}H_{25}N_5O_9$; Calculated: C 47.48% H 5.53% N 15.38%; Found: C 47.51% H 5.78% N 15.31%.

EXAMPLE 8

N,N-Dimethyl-N-cis-2-(ethoxy-carbonyl)-cyclohexenyl-formamidine-hydrochloride (1 g. 0.0038 mole) is suspended in abs. dioxane (20 ml.) and dry ammonia-gas is introduced into the mixture within 1.5 hours. The precipitated ammoniumchloride is filtered off, and the solution is evaporated to dryness. The dry residue is dissolved in chloroform and separated from the starting material on silicagel thin layer, with 8 : 2 petrolether — chloroform solvent mixture by chromatography. The hexahydroquinazoline spot is scratched from the layer and the substance is dissolved with chloroform. Thus 0.2 g. of cis-4a,5,6,7,8,8a-hexahydroquinazoline-4(3H)-on, melting at 133° to 134° C are obtained.

Analysis for $C_8H_{12}N_2O$; Calculated: C 63.13% H 7.95% N 18.41%; Found: C 63.11% H 7.84% N 18.31%.

3-(p-tolyl)-4a,5,6,7,8,8a-hexahydroquinazoline-4(3H)-on

N-p-tolyl-cis-2-amino-1-cyclohexane-carboxanilide (0.01 mole, 2.32 g.) is dissolved in chlorobenzene (40 ml.) and the solution, after the addition of ethyl-o-formiate (1.63 g.) is refluxed for 6 hours. The solvent is distilled off under reduced pressure. The residue is crystallized from petroleum ether. Thus a white, crystalline product, melting at 79° C to 82° C is obtained.

Yield: 1.25 g. (51.51%).

Analysis for $C_{15}H_{18}N_2O$ (242.32); Calculated: C 74.35% H 7.49% N 11.56%; Found: C 73.93% H 7.43% N 11.76%.

2-Phenyl-4a,5,6,7,8,8a-hexahydroquinazoline-4(3H)-on

N-butyl- or N-phenyl-cis-2-amino-1-cyclohexane-carboxamide (0.01 mole) is dissolved in 40 ml. chlorobenzene and after the addition of ethyl-phenyl-imidate (0.011 mole) the solution is refluxed for 50 hours. The solvent is distilled off under reduced pressure (2.5 Hgmm.) and the residue is crystallized from the below-identified solvents.

(a) Starting substance: N-butyl-cis-2-amino-1-cyclohexane-carboxamide

Product: White crystalline solid, melting 165° C to 167° C (from ethanol)

Yield: 73.81%

Analysis for $C_{14}H_{16}N_2O$ (228.30) Calculated: C 73.65% H 7.02% N 12.28%; Found: C 73.25% H 7.05% N 12.15%.

(b) Starting substance: N-phenyl-cis-2-amino-1-cyclohexane-carboxanilide.

Product: white, crystalline compound, melting at 165° C to 168° C (ethanol)

Yield: 69.65%

Analysis for $C_{14}H_{16}N_2O$ (228.30); Calculated: C 73.65% H 7.02% N 12.28%; Found: C 73.65% H 7.28% N 11.79%.

(c) Starting substance: cis-2-amino-1-cyclohexanecarboxamide

Product: white, crystalline compound, melting at 168° C to 170° C (ethanol).

Yield: 65.27%.

Analysis for $C_{14}H_{16}N_2O$ (228.30); Calculated: C 73.65% H 7.02% N 12.28%; Found: C 73.22% H 7.20% N 11.99%.

2-Phenyl-3-methyl-4a,5,6,7,8,8a-hexahydroquinazoline-4(3H)-on

N-Methyl-benzamide-imidachloride (0.01 mole) is dissolved in abs. acetone (20 ml.) and ethyl-hexahydroantranilate (0.02 mole) in acetone (40 ml.) is added dropwise, at 0° C. The mixture is allowed to stand at room temperature overnight, whereupon the acetone is distilled off. The base is set free on a Varion AD anion-exchanger, and the unreacted ester is distilled off under reduced pressure (2.5 Hgmm.). The residue is crystallized from petroleum ether. Melting point: 79°–82° C, yield: 38.25%.

Analysis for $C_{15}H_{18}N_2Oj$ (242.32); Calculated: C 74.36% H 7.49% N 11.56%; Found: C 74.68% H 7.38% N 11.32%.

2-(m-chlorophenyl)-cis-5,6-trimethylene-5,6-dihydropyrimidine-4(3H)-on

Following the procedure of Example 1, cis-2-amino-1-cyclopentane-carboxylic acid (12.92 g.) is boiled with ethyl-m-chloro-benzimidate (20.2 g.) for 20 hours. 17 g. of 2-(m-chlorophenyl)-cis-5,6-trimethylene-5,6-dihydro-pyrimidine-4(3H)-on are obtained. Melting point: 138° C to 140° C (ethylacetate).

Analysis for $C_{13}H_{13}ClN_2O$ Calculated: C 62.78% H 5.27% N 11.26%; Found: C 62.85% H 5.42% N 11.06%.

EXAMPLE 9

A tablet of the following composition is prepared: 2-(m-chlorophenyl)-cis-5,6-trimethylene-5,6-dihydro-

| | |
|---|---|
| pyrimidine-4-(3H)-on | 50 mg. |
| Amilopectine | 10 mg. |
| Crystalline cellulose | 60 mg. |
| Stearic acid | 12 mg. |
| Talcum | 13 mg. |
| Total weight: | 145 mg. |

The active ingredient and crystalline cellulose are admixed and homogenized in the above-given proportion. The corresponding quantities of stearinic acid and talcum are homogenized and passed through a 100-mesh sieve whereupon it is added to the above mixture and tableted under moderated pressure.

2-(m-chloro-phenyl)-5,6-5dimethylene-5,6-dihydro-pyrimidine-4(3H)-on prepared according to the method described in the last paragraph of Example 8, causes an inhibition of 39% during carragenin-induced oedema-test in mice, when applied in 6 mg./kg. p.o. dose.

The obtained inhibition is in the same order of magnitude as that caused by indomethacine. On the other hand the toxicity of the above compound of the formula I is $LD_{50} = 1600$ mg./kg. p.o., while that of the indomethacine 33 mg/kg., p.o., i.e. the therapeutic index of our compounds is more favorable than that of indomethacine.

The compounds of the present invention thus have the same utility as indomethacine in human and animal therapy in dosages equal to or up to 50 times greater than those hitherto used for indomethacine.

What we claim is:

1. A compound of the formula:

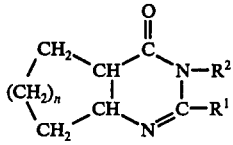

wherein
(a) $R^1$ is methyl, cyclohexyl, phenyl, m-tolyl, p-tolyl, p-tert-butylphenyl, m-trifluoromethylphenyl, m-fluorophenyl, p-fluorophenyl, m-chlorophenyl, p-chlorophenyl, m-bromophenyl, p-bromophenyl, o-hydroxyphenyl, p-methoxyphenyl, p-nitrophenyl, benzyl, p-chlorobenzyl, m,p-dimethoxyphenyl, or o-pyridyl, $R^2$ is hydrogen and $n$ is 2; or
(b) $R^1$ is phenyl, p-tert-butylphenyl, m-chlorophenyl, p-chlorophenyl, p-bromophenyl or p-nitrophenyl; $R^2$ is hydrogen and $n$ is 3; or
(c) $R^1$ is phenyl or m-chlorophenyl, $R^2$ is hydrogen and $n$ is 1; or
(d) $R^1$ is methyl, $R^2$ is p-tolyl or p-ethoxyphenyl, and $n$ is 2; or
(e) $R^1$ is ethyl, $R^2$ is m-pyridyl or p-tolyl; and $n$ is 2; or
(f) $R^1$ is phenyl, $R^2$ is methyl, phenyl or p-tolyl and $n$ is 2.

2. The compound defined in claim 1 wherein $R^1$ is methyl, $R^2$ is hydrogen and $n$ is 2.

3. The compound defined in claim 1 wherein $R^1$ is cyclohexyl, $R^2$ is hydrogen and $n$ is 2.

4. The compound defined in claim 1 wherein $R^1$ is phenyl, $R^2$ is hydrogen and $n$ is 2.

5. The compound defined in claim 1 wherein $R^1$ is m-tolyl, $R^2$ is hydrogen and $n$ is 2.

6. The compound defined in claim 1 wherein $R^1$ is p-tolyl, $R^2$ is hydrogen and $n$ is 2.

7. The compound defined in claim 1 wherein $R^1$ is p-tert-butylphenyl, $R^2$ is hydrogen and $n$ is 2.

8. The compound defined in claim 1 wherein $R^1$ is m-trifluoromethylphenyl, $R^2$ is hydrogen and $n$ is 2.

9. The compound defined in claim 1 wherein $R^1$ is m-fluorophenyl, $R^2$ is hydrogen and $n$ is 2.

10. The compound defined in claim 1 wherein $R^1$ is p-fluorophenyl, $R^2$ is hydrogen and $n$ is 2.

11. The compound defined in claim 1 wherein $R^1$ is m-chlorophenyl, $R^2$ is hydrogen and $n$ is 2.

12. The compound defined in claim 1 wherein $R^1$ is p-chlorophenyl, $R^2$ is hydrogen and $n$ is 2.

13. The compound defined in claim 1 wherein $R^1$ is m-bromophenyl, $R^2$ is hydrogen and $n$ is 2.

14. The compound defined in claim 1 wherein $R^1$ is p-bromophenyl, $R^2$ is hydrogen and $n$ is 2.

15. The compound defined in claim 1 wherein $R^1$ is o-hydroxyphenyl, $R^2$ is hydrogen and $n$ is 2.

16. The compound defined in claim 1 wherein $R^1$ is p-methoxyphenyl, $R^2$ is hydrogen and $n$ is 2.

17. The compound defined in claim 1 wherein $R^1$ is p-nitrophenyl, $R^2$ is hydrogen and $n$ is 2.

18. The compound defined in claim 1 wherein $R^1$ is benzyl, $R^2$ is hydrogen and $n$ is 2.

19. The compound defined in claim 1 wherein $R^1$ is p-chlorobenzyl, $R^2$ is hydrogen and $n$ is 2.

20. The compound defined in claim 1 wherein $R^1$ is m,p-dimethoxyphenyl, $R^2$ is hydrogen and $n$ is 2.

21. The compound defined in claim 1 wherein $R^1$ is o-pyridyl, $R^2$ is hydrogen and $n$ is 2.

22. The compound defined in claim 1 wherein $R^1$ is phenyl, $R^2$ is hydrogen and $n$ is 3.

23. The compound defined in claim 1 wherein $R^1$ is p-tert-butylphenyl, $R^2$ is hydrogen and $n$ is 3.

24. The compound defined in claim 1 wherein $R^1$ is m-chlorophenyl, $R^2$ is hydrogen and $n$ is 3.

25. The compound defined in claim 1 wherein $R^1$ is p-chlorophenyl, $R^2$ is hydrogen and $n$ is 3.

26. The compound defined in claim 1 wherein $R^1$ is p-bromophenyl, $R^2$ is hydrogen and $n$ is 3.

27. The compound defined in claim 1 wherein $R^1$ is p-nitrophenyl, $R^2$ is hydrogen and $n$ is 3.

28. The compound defined in claim 1 wherein $R^1$ is phenyl, $R^2$ is hydrogen, and $n$ is 1.

29. The compound defined in claim 1 wherein $R^1$ is m-chlorophenyl, $R^2$ is hydrogen and $n$ is 1.

30. The compound defined in claim 1 wherein $R^1$ is methyl, $R^2$ is p-tolyl and $n$ is 2.

31. The compound defined in claim 1 wherein $R^1$ is methyl, $R^2$ is p-ethoxyphenyl and $n$ is 2.

32. The compound defined in claim 1 wherein $R^1$ is ethyl, $R^2$ is m-pyridyl and $n$ is 2.

33. The compound defined in claim 1 wherein $R^1$ is ethyl, $R^2$ is p-tolyl and $n$ is 2.

34. The compound defined in claim 1 wherein $R^1$ is phenyl, $R^2$ is methyl and $n$ is 2.

35. The compound defined in claim 1 wherein $R^1$ is phenyl, $R^2$ is phenyl and $n$ is 2.

36. The compound defined in claim 1 wherein $R^1$ is phenyl, $R^2$ is p-tolyl and $n$ is 2.

37. An antiedema composition which comprises an effective amount of the compound defined in claim 1 with at least one pharmaceutically acceptable inert carrier or diluent.

38. A method of treating edema in animals which comprises the step of orally administering an effective amount of the compound defined in claim 1.

* * * * *